US012127824B2

(12) United States Patent
Hoshino et al.

(10) Patent No.: US 12,127,824 B2
(45) Date of Patent: Oct. 29, 2024

(54) BLOOD FLOW MEASUREMENT DEVICE

(71) Applicant: NeU Corporation, Tokyo (JP)

(72) Inventors: Takeshi Hoshino, Tokyo (JP); Ryuta Kawashima, Tokyo (JP); Kiyoshi Hasegawa, Tokyo (JP); Takushige Katsura, Tokyo (JP)

(73) Assignee: NeU Corporation, Tokyo (JP)

( * ) Notice: Subject to any disclaimer, the term of this patent is extended or adjusted under 35 U.S.C. 154(b) by 644 days.

(21) Appl. No.: 17/282,074

(22) PCT Filed: Oct. 2, 2019

(86) PCT No.: PCT/JP2019/038968
§ 371 (c)(1),
(2) Date: Apr. 1, 2021

(87) PCT Pub. No.: WO2020/071443
PCT Pub. Date: Apr. 9, 2020

(65) Prior Publication Data
US 2021/0386301 A1   Dec. 16, 2021

(30) Foreign Application Priority Data
Oct. 2, 2018 (JP) .................. 2018-187719

(51) Int. Cl.
*A61B 5/026* (2006.01)
*A61B 5/00* (2006.01)
(52) U.S. Cl.
CPC .......... *A61B 5/0261* (2013.01); *A61B 5/0004* (2013.01); *A61B 5/6803* (2013.01);
(Continued)
(58) Field of Classification Search
CPC ................ A61B 5/0261; A61B 5/0004; A61B 2562/0238
See application file for complete search history.

(56) References Cited

U.S. PATENT DOCUMENTS

| 7,524,291 B1 | 4/2009 | Nakagawara |
| 2011/0295128 A1 | 12/2011 | Yuasa et al. |

(Continued)

FOREIGN PATENT DOCUMENTS

| JP | 2000-166884 A | 6/2000 |
| JP | 2005-130969 A | 5/2005 |

(Continued)

OTHER PUBLICATIONS

International Search Report of PCT/JP2019/038968 dated Dec. 17, 2019.

*Primary Examiner* — Jason M Ip
(74) *Attorney, Agent, or Firm* — MATTINGLY & MALUR, PC

(57) ABSTRACT

A blood flow measurement device easily measures the blood flow of a user, and includes a first body portion, a second body portion, and a hinge. The first body portion includes a first casing having a first bottom face, a light source that emits near-infrared radiation from the first bottom face to the outside of the first casing, and a first light reception unit that receives the near-infrared radiation from the first bottom face side on the outside of the first casing. The second body portion includes a second casing having a second bottom face, and a second light reception unit that receives the near-infrared radiation from the second bottom face side on the outside of the second casing. The hinge joins the first body portion to the second body portion so as to make an angle formed by the first bottom face and the second bottom face variable.

4 Claims, 15 Drawing Sheets

(52) U.S. Cl.
CPC .......... *A61B 5/6824* (2013.01); *A61B 5/6828* (2013.01); *A61B 2560/04* (2013.01); *A61B 2562/0238* (2013.01)

(56) References Cited

U.S. PATENT DOCUMENTS

| | | | |
|---|---|---|---|
| 2017/0027511 A1* | 2/2017 | Connor | A61B 5/0537 |
| 2017/0086688 A1 | 3/2017 | Masuda | |
| 2019/0038156 A1 | 2/2019 | Kinoshita et al. | |

FOREIGN PATENT DOCUMENTS

| | | |
|---|---|---|
| JP | 2009-119151 A | 6/2009 |
| JP | 2009-240511 A | 10/2009 |
| JP | 2011-244938 A | 12/2011 |
| JP | 2017-060659 A | 3/2017 |
| JP | 2017-063893 A | 4/2017 |
| JP | 2017-189508 A | 10/2017 |
| WO | 2017/170804 A1 | 10/2017 |

\* cited by examiner

FIG.8
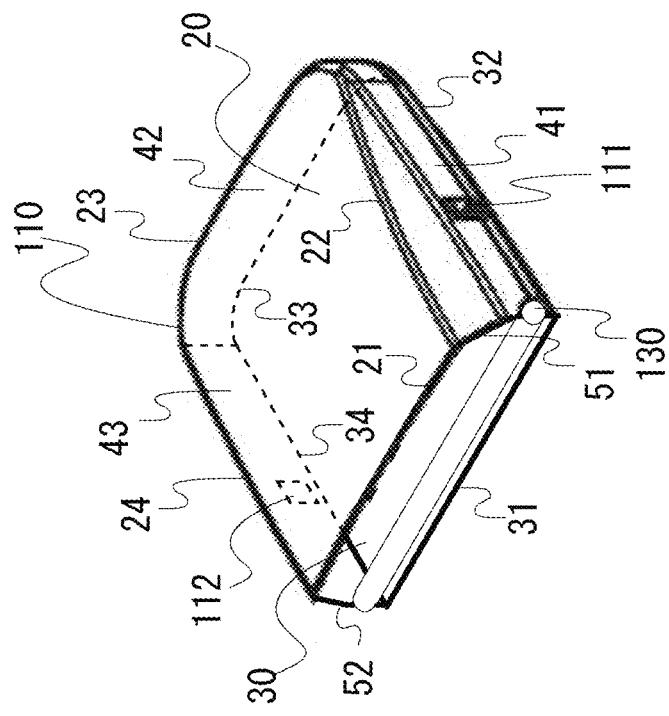
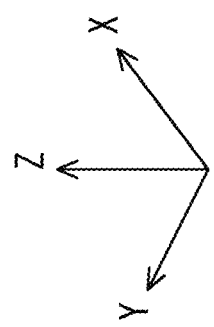

BLOOD FLOW MEASUREMENT DEVICE

TECHNICAL FIELD

The present invention relates to a blood flow measurement device.

BACKGROUND ART

As aging advances in Japan, future increases in medical expenses for elderly people are predicted. To prevent increases in social costs, including medical expenses, it is necessary for healthy people to take illness prevention measures. In particular, brain training is required on a daily basis in order to maintain good brain health.

In a measurement system provided in the prior art, a cerebral blood flow measurement device known as a headset is provided with a near-infrared radiation emission unit and a near-infrared radiation detection unit, variation in the blood flow on the surface of the brain is detected, and by processing the detected data using a data processing device, information indicating brain activity is acquired. Using this measurement system, brain activity occurring while a user (a subject) performs various actions is measured.

CITATION LIST

Patent Literature

[PTL 1] Japanese Patent Application Publication No. 2000-166884
[PTL 2] Japanese Patent Application Publication No. 2011-244938
[PTL 3] Japanese Patent Application Publication No. 2017-63893
[PTL 4] Japanese Patent Application Publication No. 2017-189508
[PTL 5] Japanese Patent Application Publication No. 2005-130969

SUMMARY OF INVENTION

Technical Problem

To maintain good health, elderly people ideally perform brain training at home while measuring cerebral blood flow. However, it is not practical for elderly people to measure cerebral blood flow at home due to the size of the cerebral blood flow measurement device and so on.

An object of the present invention is to provide a blood flow measurement device with which the blood flow of a user can be measured easily.

Solution to Problem

To solve the problem described above, the following means is employed.

More specifically, a first aspect is a blood flow measurement device including a first body portion, a second body portion, and a hinge, wherein
the first body portion includes a first casing having a first bottom face, a light source that emits near-infrared radiation from the first bottom face to the outside of the first casing, and a first light reception unit that receives the near-infrared radiation from the first bottom face side on the outside of the first casing,
the second body portion includes a second casing having a second bottom face, and a second light reception unit that receives the near-infrared radiation from the second bottom face side on the outside of the second casing, and
the hinge joins the first body portion to the second body portion so as to make an angle formed by the first bottom face and the second bottom face variable.

The aspects of the disclosure may be realized by executing a program on an information processing device. In other words, the configurations of the disclosure can be specified as a program for causing an information processing device to execute processing for executing the means of the aspect described above or a computer-readable recording medium on which the program is recorded. The configurations of the disclosure may also be specified by a method used by an information processing device to execute processing for executing the means described above. The configurations of the disclosure may also be specified as a system including an information processing device that performs processing for executing the means described above.

The processing steps described in the program may naturally be performed in chronological order in the order in which the steps are described, but the processing steps do not necessarily have to be performed in chronological order and may be executed in parallel or individually. Some of the steps described in the program may be omitted.

Advantageous Effects of Invention

According to the present invention, it is possible to provide a blood flow measurement device with which the blood flow of a user can be measured easily.

BRIEF DESCRIPTION OF DRAWINGS

FIG. 8 is a perspective view showing a first casing 110 and a hinge 130 of the blood flow measurement device 10 from above.

DESCRIPTION OF EMBODIMENTS

An embodiment will be described below with reference to the figures. The configurations of the embodiment are examples, and the configuration of the invention is not limited to the specific configurations of the embodiment of the disclosure. When implementing the invention, specific configurations corresponding to those of the embodiment may be employed as appropriate.

Embodiment

Example Functional Configuration

Figure 1:
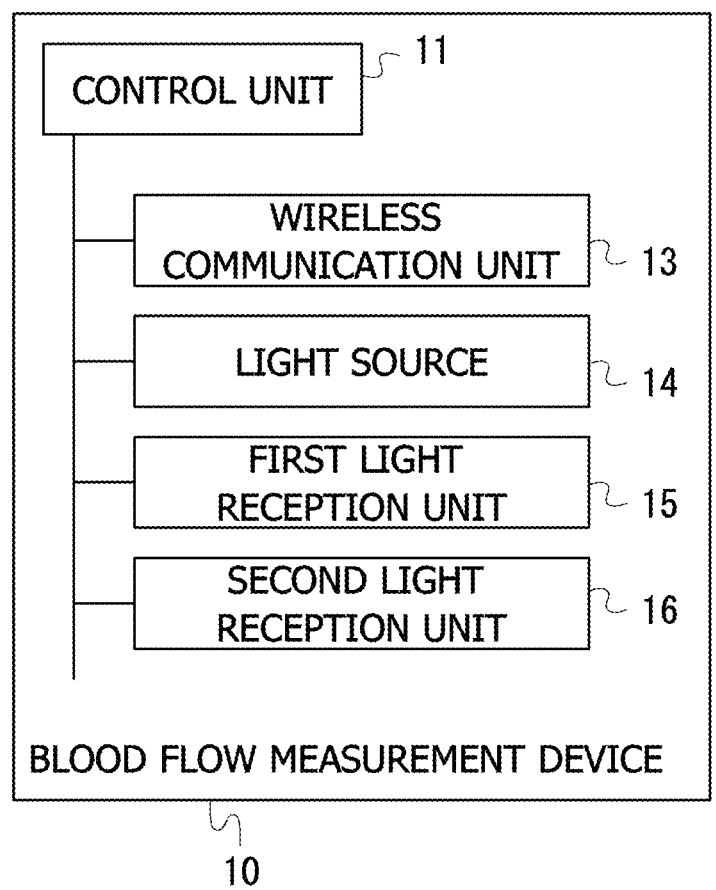
FIG. 1 is a view showing an example functional configuration of a blood flow measurement device 10.

FIG. 1 is a view showing an example functional configuration of a blood flow measurement device 10. The blood flow measurement device 10 includes, as aspects of information processing, a control unit 11, a wireless communication unit 13, a light source 14, a first light reception unit 15, and a second light reception unit 16. The control unit 11 controls measurement and communication by the blood flow measurement device 10. For example, the control unit 11 includes a processor, such as a CPU (Central Processing Unit) or a DSP (Digital Signal Processor), and a memory, and executes processing using a computer program, firmware, or the like, which is expanded on the memory so as to be executable. Note that the control unit 11 may also be constituted by a dedicated hardware circuit, an FPGA (Field Programmable Gate Array), or the like that activates the wireless communication unit 13, the light source 14, the first light reception unit 15, and the second light reception unit 16 and executes processing cooperatively with the respective constituent elements. The control unit 11 may also be a mixture of a CPU, a DSP, a dedicated hardware circuit, and so on. The blood flow measurement device 10 is structured so as to be mounted on the head, arm, leg, or the like of a user and fixed to the user.

The wireless communication unit 13 is connected to the control unit 11, the light source 14, the first light reception unit 15, and the second light reception unit 16 by a predetermined interface. Note, however, that the wireless communication unit 13 may be configured to acquire data from the first light reception unit 15 and the second light reception unit 16 via the control unit 11. The wireless communication unit 13 communicates with another information processing device or the like over a network. The wireless communication unit 13 is an example of transferring means. Note that in the blood flow measurement device 10, there are no limitations on the wireless interface standard of the wireless communication unit 13.

By embedding an identifier identifying the blood flow measurement device 10 in a header part of a communication header or a user data part (a payload part) of communication data during communication over the network, the other information processing device can identify the user (the subject).

Further, in the blood flow measurement device 10, a communication unit that communicates using a wire may be provided instead of the wireless communication unit 13 or alongside the wireless communication unit 13. In other words, the blood flow measurement device 10 and the other information processing device may be connected by a wired communication interface. In this case, there are no limitations on the wired communication interface, and various interfaces, such as a USB (Universal Serial Bus) or PCI Express (registered trademark), can be used in accordance with the application of the blood flow measurement device 10.

The light source 14 includes a near-infrared light source that emits near-infrared radiation. Examples of near-infrared light sources include an LED (Light Emitting Diode), an infrared lamp, and so on. The light source 14 irradiates the body (the head, the arm, the leg, or the like) of the user with near-infrared radiation. The emitted near-infrared radiation is partially absorbed and scattered near the cerebral cortex of the brain or near a blood vessel in the arm or the like. The scattered near-infrared radiation is received by the first light reception unit 15 and the second light reception unit 16 and converted into an electric signal. Blood flow through the cerebral cortex of the brain differs according to brain activity, for example. As a result, the amount of hemoglobin bound to oxygen in the blood and the amount of hemoglobin not bound to oxygen vary in each part of the cerebral cortex. The absorption characteristic or the scattering characteristic of the near-infrared radiation in the vicinity of the cerebral cortex varies in response to variation in the amount of hemoglobin, variation in the amount of oxygen, and so on.

The first light reception unit 15 and the second light reception unit 16 each include a light reception portion for receiving the near-infrared radiation. The light reception portion includes a photoelectric element such as a photodiode or a phototransistor, an amplifier, and an AD (Analog Digital) converter. The first light reception unit 15 and the second light reception unit 16 convert the near-infrared radiation, the light amount of which varies in accordance with variation in a near-infrared absorption rate or a near-infrared transmittance corresponding to the state of blood flow near the cerebral cortex or the like, into an electric signal and output the electric signal. The first light reception unit 15 and the second light reception unit 16 are examples of a detection unit. Variation in the blood flow and the pulse rate can be calculated from the information detected by the first light reception unit 15 and the second light reception unit 16. The pulse rate corresponds to the heart rate. A distance from the light source 14 to the first light reception unit 15 differs from a distance from the light source 14 to the second light reception unit 16. By making the distances different, information about the blood flow at different depths from the surface of the body can be acquired.

Example Structure

Figure 2:
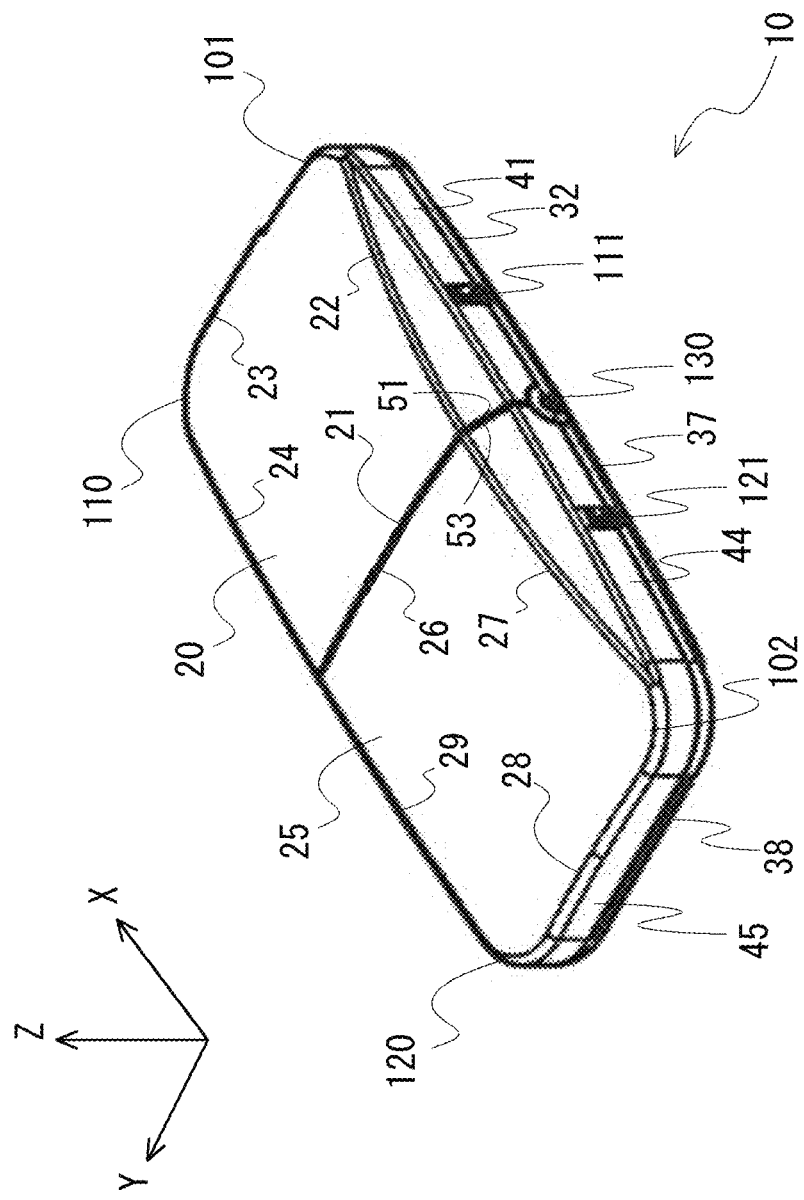
FIG. 2 is a perspective view showing the outer appearance of the blood flow measurement device 10 from above.
Figure 3:
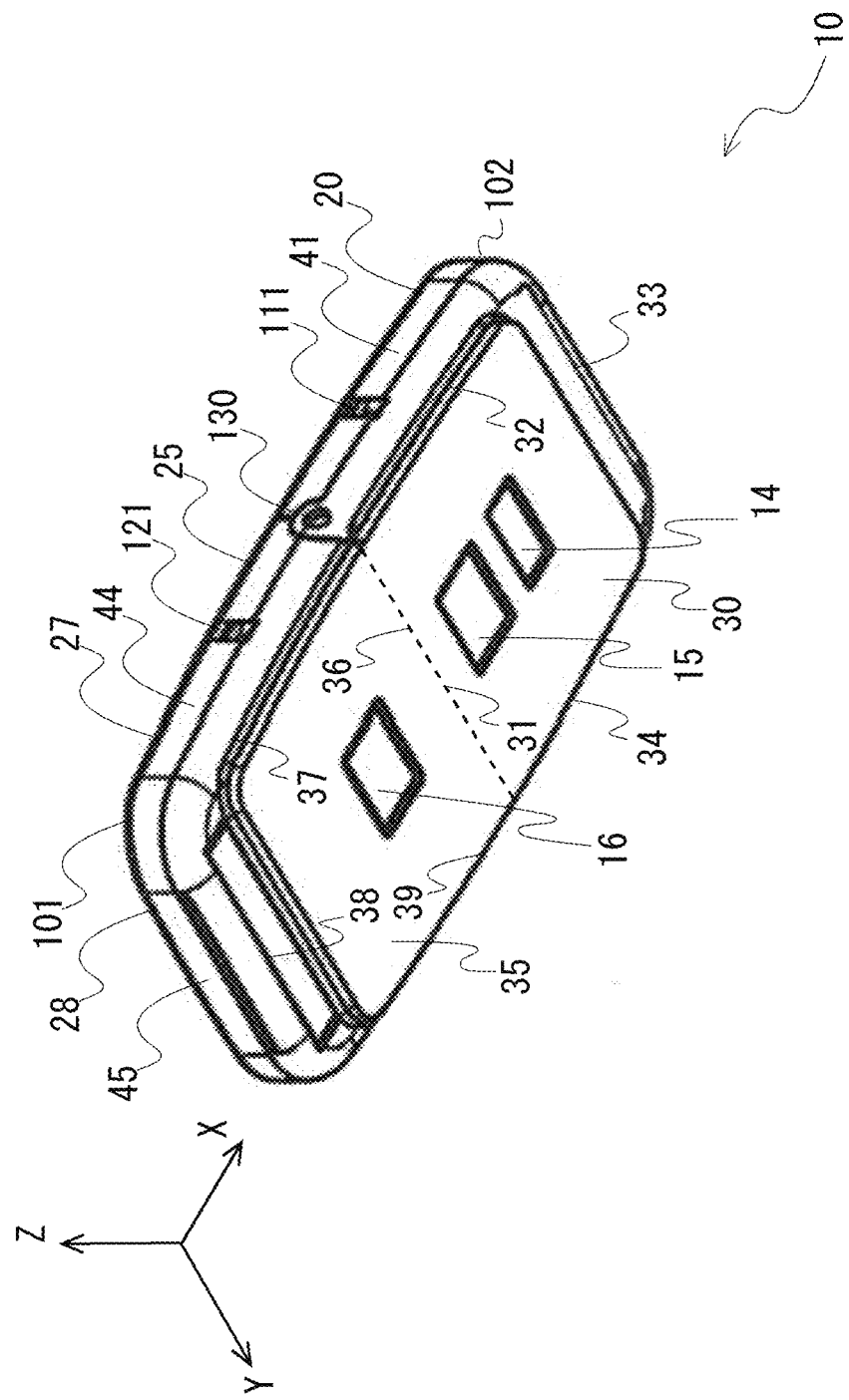
FIG. 3 is a perspective view showing the outer appearance of the blood flow measurement device 10 from below.
Figure 4:
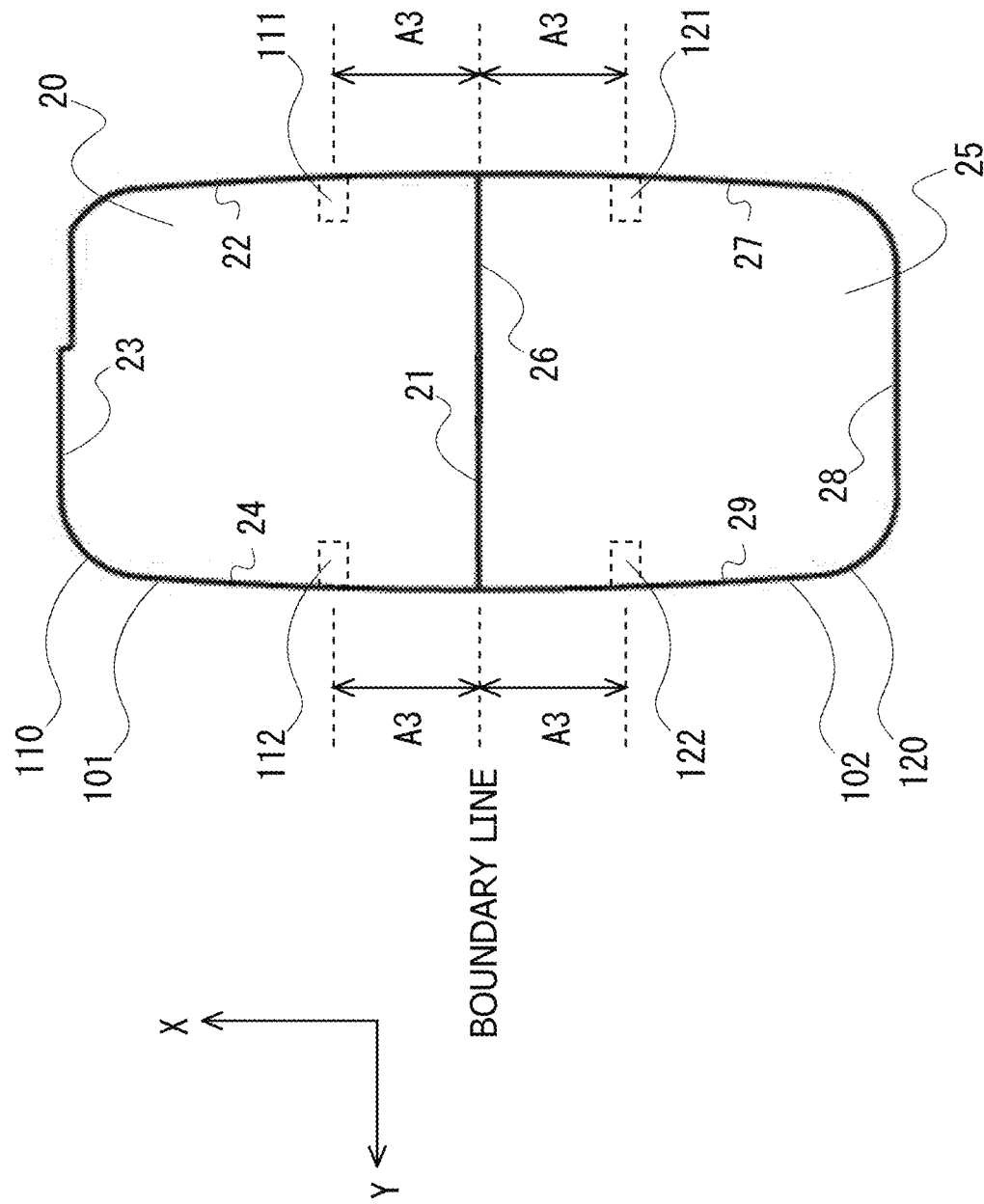
FIG. 4 is a plan view showing the outer appearance of the blood flow measurement device 10 from above.
Figure 5:
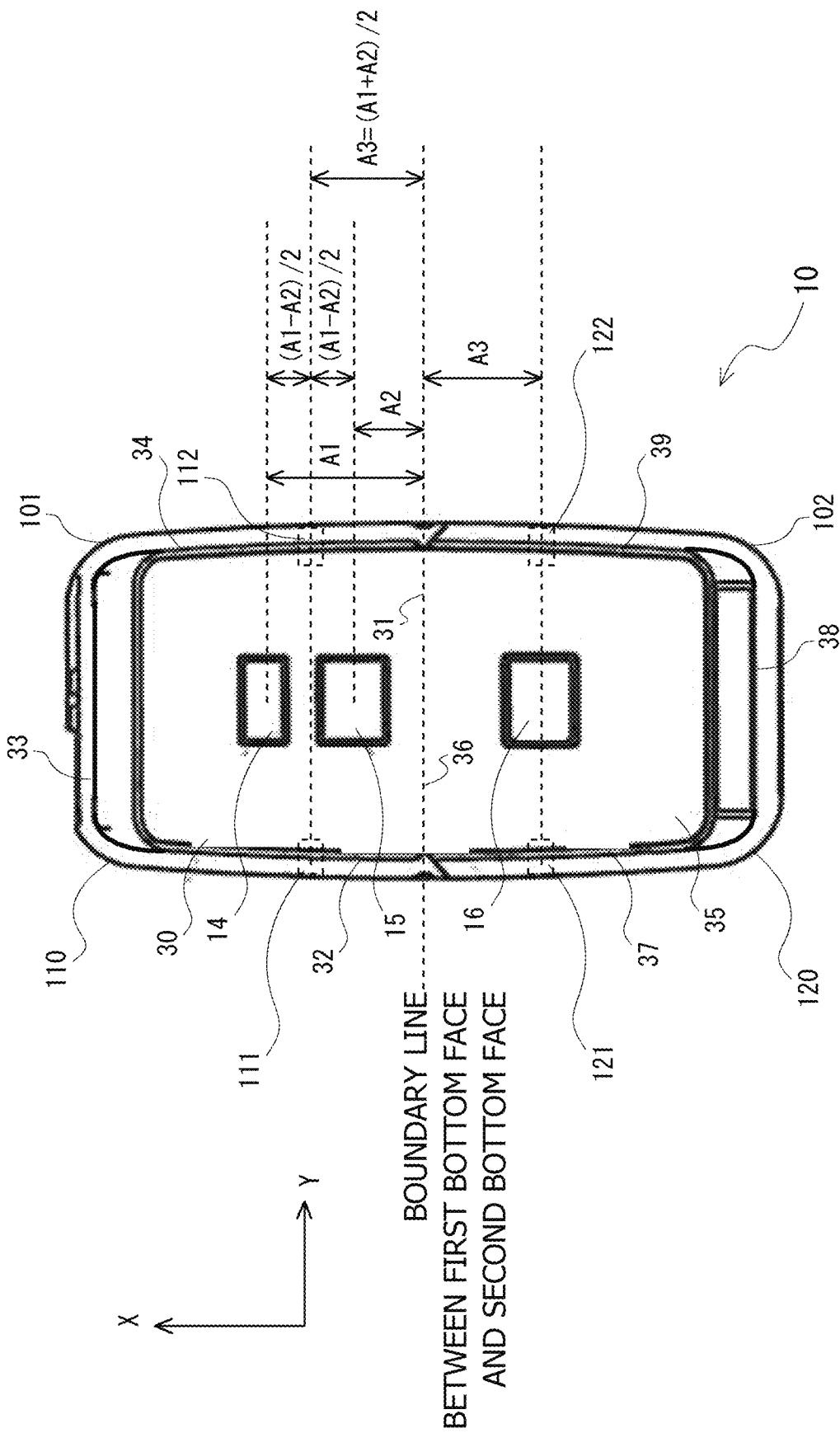
FIG. 5 is a plan view showing the outer appearance of the blood flow measurement device 10 from below.
Figure 6:
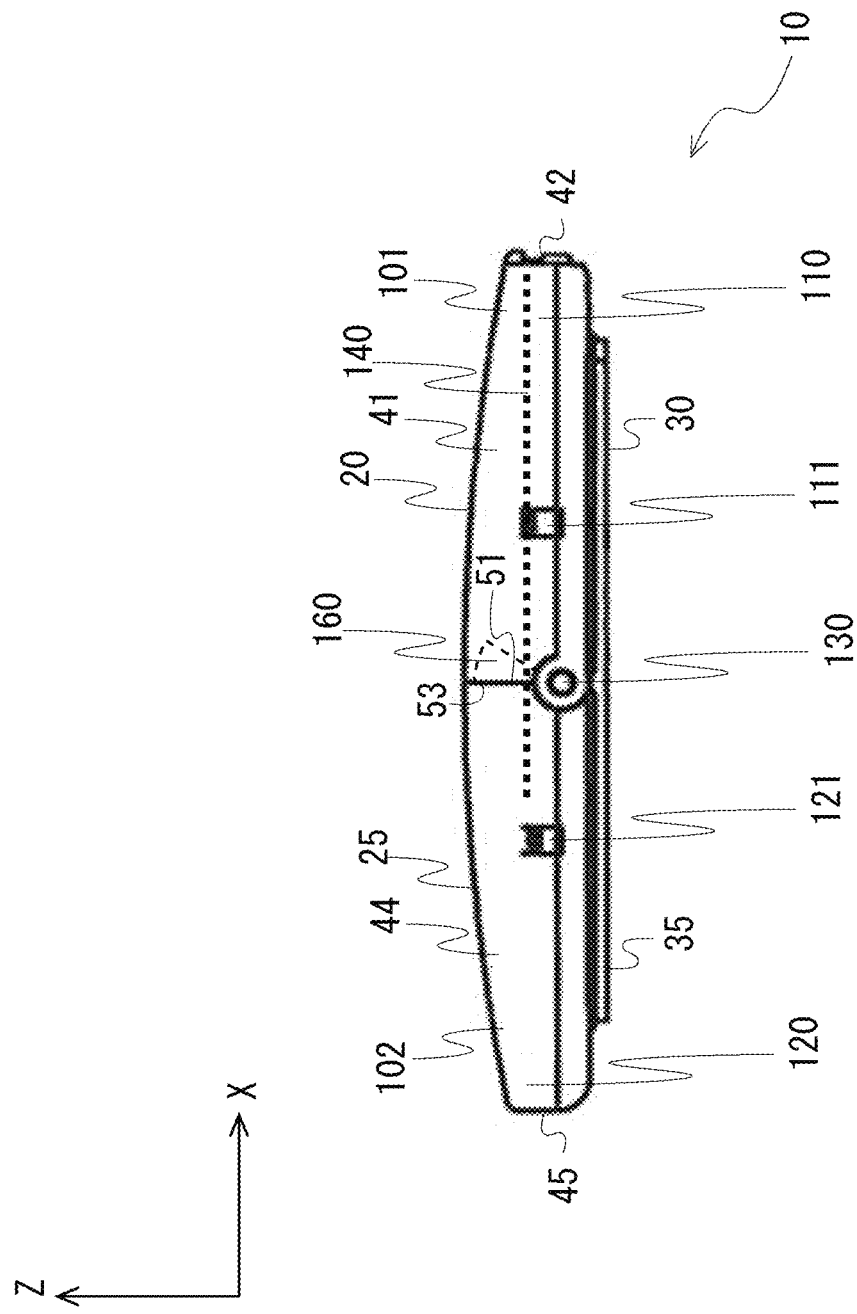
FIG. 6 is a plan view showing the outer appearance of the blood flow measurement device 10 from the front.
Figure 7:
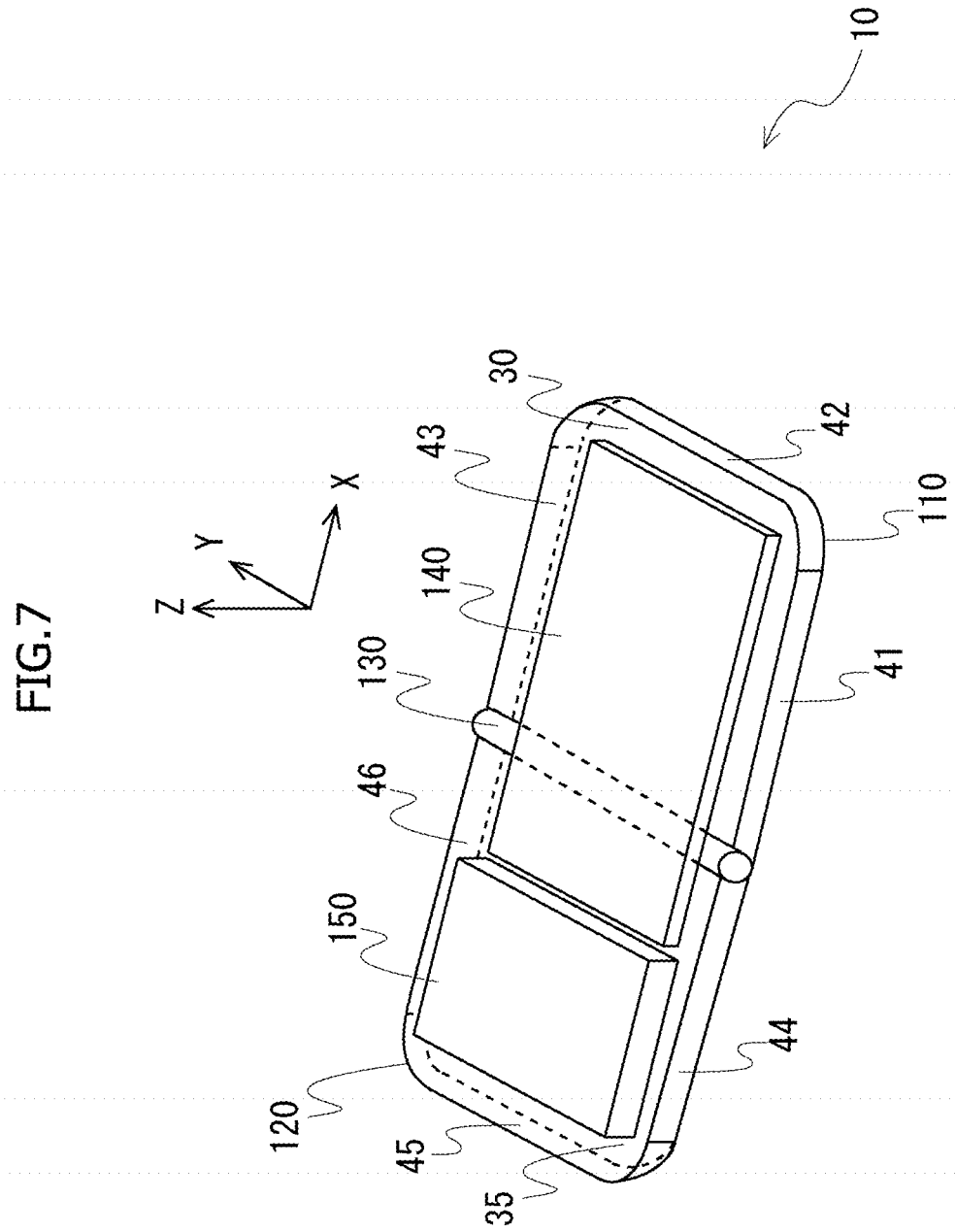
FIG. 7 is a perspective view showing an example of the internal structure of the blood flow measurement device 10.
Figure 9:
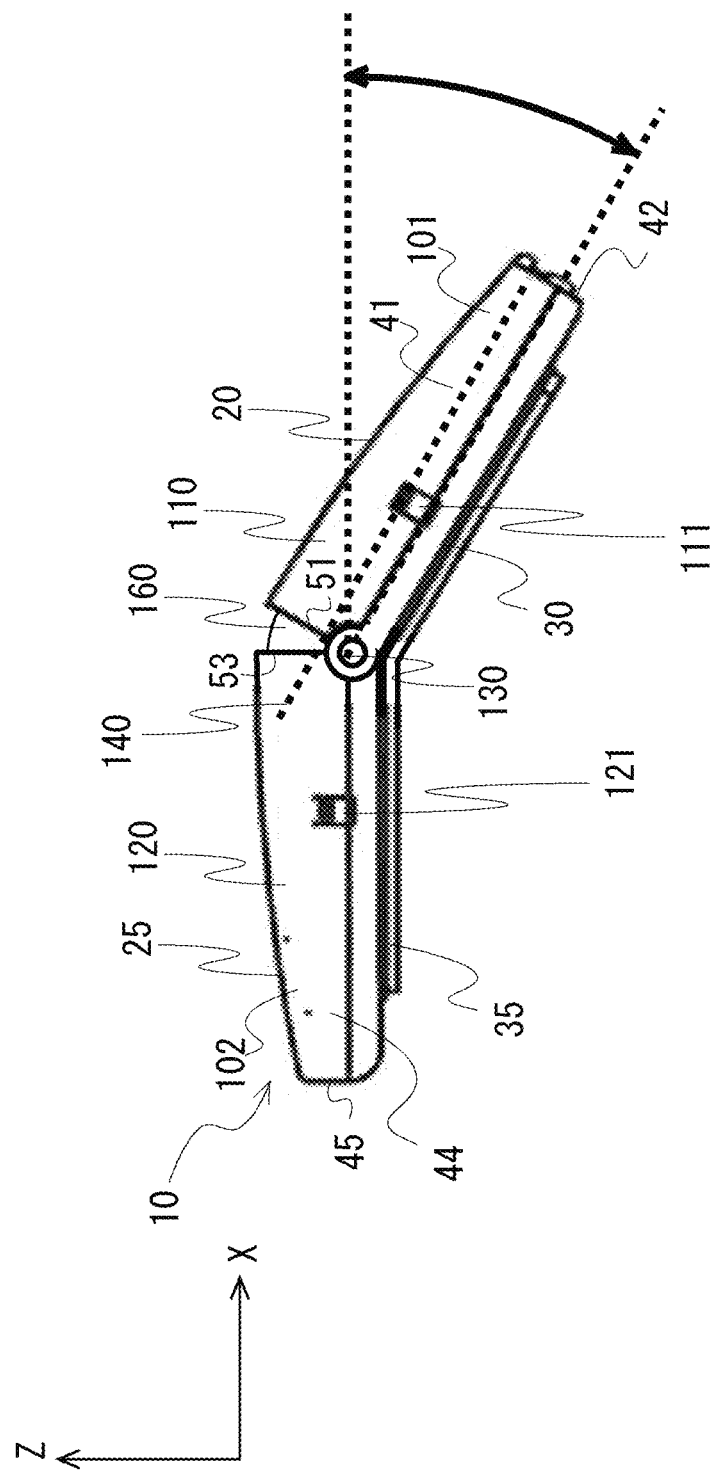
FIG. 9 is a plan view showing an example in which a first body portion 101 of the blood flow measurement device 10 has been rotated relative to a second body portion 102.

FIGS. 2 to 9 are views showing an example structure of the blood flow measurement device 10. FIG. 2 is a perspective view showing the outer appearance of the blood flow measurement device 10 from above. FIG. 3 is a perspective view showing the outer appearance of the blood flow measurement device 10 from below. FIG. 4 is a plan view showing the outer appearance of the blood flow measurement device 10 from above. FIG. 5 is a plan view showing the outer appearance of the blood flow measurement device 10 from below. FIG. 6 is a plan view showing the outer appearance of the blood flow measurement device 10 from the front. FIG. 7 is a perspective view showing an example of the internal structure of the blood flow measurement device 10. FIG. 8 is a perspective view showing a first casing 110 and a hinge 130 of the blood flow measurement device 10 from above. FIG. 9 is a plan view showing an example in which a first body portion 101 of the blood flow measurement device 10 has been rotated relative to a second body portion 102.

As shown in FIG. 2 and so on, the blood flow measurement device 10 includes the first body portion 101, the second body portion 102, the hinge 130, a substrate 140, a battery 150, and a cover portion 160. The first body portion 101 includes the first casing 110, the light source 14, and the first light reception unit 15. The second body portion 102 includes a second casing 120 and the second light reception unit 16. The casings will also be referred to as housings.

As shown in FIG. 8 and so on, the first casing 110 has a first upper face 20, a first bottom face 30, a first upper face 20, a right side face 41, an upper side face 42, and a left side face 43. The right side face 41 and the left side face 43 oppose each other. As shown in FIG. 4, on a plan view (a top view) seen from above (the first upper face 20 side), a lower-side edge of a rectangle forming the first upper face 20 in a case where the first casing 110 is viewed on top of the second casing 120 is set as a lower edge 21, a right-side edge is set as a right edge 22, an upper-side edge is set as an upper edge 23, and a left-side edge is set as a left edge 24. Similarly, as shown in FIG. 8 and so on, a lower-side edge of a rectangle forming the first bottom face 30 when seen from above is set as a lower edge 31, a right-side edge is set as a right edge 32, an upper-side edge is set as an upper edge 33, and a left-side edge is set as a left edge 34. The lower edge 21 of the first upper face 20 and the lower edge 31 of the first bottom face 30 are the edges on the second casing 120 side. The right side face 41 of the first casing 110 stands upright from the right edge 32 of the first bottom face 30 substantially at a right angle to the first bottom face 30 and is connected to the right edge 22 of the first upper face 20. The edge of the right side face 41 on the second casing 120 side is set as a left edge 51. The upper side face 42 of the first casing 110 stands upright from the upper edge 33 of the first bottom face 30 substantially at a right angle to the first bottom face 30 and is connected to the upper edge 23 of the first upper face 20. The left side face 43 of the first casing 110 stands upright from the left edge 34 of the first bottom face 30 substantially at a right angle to the first bottom face 30 and is connected to the left edge 24 of the first upper face 20. The edge of the left side face 43 on the second casing 120 side is set as a right edge 52. The right side face 41, the upper side face 42, and the left side face 43 of the first casing 110 may be planar surfaces, curved surfaces, bent surfaces, and so on. An opening portion of the first casing 110 is formed by the lower edge 31 of the first bottom face 30, the left edge 51 of the right side face 41, the lower edge 21 of the first upper face 20, and the right edge 52 of the left side face 43. The right side face 41 and the left side face 43 are respectively examples of a first right side face and a first left side face.

Note that in this embodiment, the sides seen from the paper surface in FIG. 5, or in other words planes oriented in a Z axis direction on the virtual coordinate system used in FIGS. 2 to 8, are set as the first bottom face 30 and a second bottom face 35. The first bottom face 30 and the second bottom face 35 may be set as the faces that contact the human body that is to be subjected to blood flow measurement.

The second casing 120, similarly to the first casing 110, has a second upper face 25, the second bottom face 35, a right side face 44, a lower side face 45, and a left side face 46. The right side face 44 and the left side face 46 oppose each other. As shown in FIG. 4, on a plan view (a top view) seen from above (the second upper face 25 side), an upper-side edge of a rectangle forming the second upper face 25 in a case where the first casing 110 is viewed on top of the second casing 120 is set as an upper edge 26, a right-side edge is set as a right edge 27, a lower-side edge is set as a lower edge 28, and a left-side edge is set as a left edge 29. Similarly, an upper-side edge of a rectangle forming the second bottom face 35 when seen from above is set as an upper edge 36, a right-side edge is set as a right edge 37, a lower-side edge is set as a lower edge 38, and a left-side edge is set as a left edge 39. The upper edge 26 of the second upper face 25 and the upper edge 36 of the second bottom face 35 are the edges on the first casing 110 side. The right side face 44 of the second casing 120 stands upright from the right edge 37 of the second bottom face 35 substantially at a right angle to the second bottom face 35 and is connected to the right edge 27 of the second upper face 25. The edge of the right side face 44 on the first casing 110 side is set as a right edge 53. The lower side face 45 of the second casing 120 stands upright from the lower edge 38 of the second bottom face 35 substantially at a right angle to the second bottom face 35 and is connected to the lower edge 28 of the second upper face 25. The left side face 46 of the second casing 120 stands upright from the left edge 39 of the second bottom face 35 substantially at a right angle to the second bottom face 35 and is connected to the left edge 29 of the second upper face 25. The edge of the left side face 46 on the first casing 110 side is set as a left edge 54. The right side face 44, the lower side face 45, and the left side face 46 of the second casing 120 may be planar surfaces, curved surfaces, bent surfaces, and so on. An opening portion of the second casing 120 is formed by the upper edge 36 of the second bottom face 35, the right edge 53 of the right side face 44, the upper edge 26 of the second upper face 25, and the left edge 54 of the left side face 46. The right side face 44 and the left side face 46 are respectively examples of the second right side face and the second left side face.

The first casing 110 and the second casing 120 are formed from a resin such as plastic, for example. The first bottom face 30 of the first casing 110 and the second bottom face 35 of the second casing 120 can also be referred to together as the bottom face of the blood flow measurement device 10. The bottom face of the blood flow measurement device 10 contacts the body of the user. Hence, a soft member (a resin such as urethane, rubber, fabric, or the like) may be adhered to the bottom face of the blood flow measurement device 10.

As shown in FIG. 2 and so on, a normal direction of the second bottom face 35 of the second casing 120 is set as the Z axis direction, a longitudinal direction of the blood flow measurement device 10, which is orthogonal to the Z axis direction, is set as an X axis direction, and a latitudinal direction of the blood flow measurement device 10, which is orthogonal to the Z axis direction, is set as a Y axis direction.

The opening portion of the first casing 110 and the opening portion of the second casing 120 are aligned so as to form a single enclosed space. As shown in FIG. 7, the substrate 140, the battery 150, and so on are disposed in this enclosed space. When aligning the respective opening portions, the lower edge 21 of the first upper face 20, the left edge 51 of the right side face 41, the lower edge 31 of the first bottom face 30, and the right edge 52 of the left side face 43 in the first casing 110 are aligned respectively with the upper edge 26 of the second upper face 25, the right edge 53 of the right side face 44, the upper edge 36 of the second bottom face 35, and the left edge 54 of the left side face 46 in the second casing 120.

The first body portion 101 and the second body portion 102 are joined by the hinge 130. The hinge 130 includes a rotary shaft, a member provided on the first bottom face 30 of the first casing 110 in order to support the rotary shaft, and a member provided on the second bottom face 35 of the second casing 120 in order to support the rotary shaft. The rotary shaft of the hinge 130 is provided parallel to the Y axis direction near the lower edge 31 of the first bottom face 30 of the first casing 110 and the upper edge 36 of the second bottom face 35 of the second casing 120. The hinge 130 makes the angle formed by the first bottom face 30 and the second bottom face 35 variable.

As shown in FIG. 9, the first body portion 101 rotates relative to the second body portion 102 using the rotary shaft of the hinge 130 as an axis. The rotatable angle is between 0 degrees and 30 degrees, for example. In other words, when the first body portion 101 rotates, the angle formed by the first bottom face 30 of the first casing 110 and the second bottom face 35 of the second casing 120 varies from 0 degrees to 30 degrees, for example. A state in which the formed angle is 0 degrees is set as an initial state. When the first body portion 101 rotates such that the formed angle increases from 0 degrees, the lower edge 21 of the first upper face 20 of the first casing 110 and the upper edge 26 of the second upper face 25 of the second casing 120 separate from each other. Furthermore, at this time, the left edge 51 of the right side face 41 and the right edge 52 of the left side face 43 in the first casing 110 separate from the right edge 53 of the right side face 44 and the left edge 54 of the left side face 46 in the second casing 120. As shown in FIG. 9, the cover portion 160 is provided to ensure that the interior (the enclosed space) of the blood flow measurement device 10 is invisible from the outside at this time. The cover portion 160 has a planar shape and is disposed to project in the direction of the first casing 110 from the upper edge 26 of the second upper face 25, the right edge 53 of the right side face 44, and the left edge 54 of the left side face 46, which form the opening portion of the second casing 120. When the cover portion 160 is not provided, the interior of the blood flow measurement device 10 is visible from the outside, making it easy for dust and so on to infiltrate the interior, and as a result, the blood flow measurement device 10 may malfunction.

As shown in FIGS. 3, 5, and so on, the light source 14 and the first light reception unit 15 are provided on the first bottom face 30 of the first casing 110. The second light reception unit 16 is provided on the second bottom face 35 of the second casing 120. The light source 14 emits near-infrared radiation from the first bottom face 30 to the outside of the first casing 110. The first light reception unit 15 receives the near-infrared radiation from the first bottom face 30 side on the outside of the first casing 110. The second light reception unit 16 receives the near-infrared radiation from the second bottom face 35 side on the outside of the second casing 120. The light source 14, the first light reception unit 15, and the second light reception unit 16 are disposed so that the center of the light source 14, the center of the first light reception unit 15, and the center of the second light reception unit 16 exist on a straight line that is parallel to the X axis. A boundary line between the first bottom face 30 and the second bottom face 35 is parallel to the Y axis direction. A distance from the boundary line between the first bottom face 30 and the second bottom face 35 to the center of the light source 14 is set as A1. A distance from the boundary line between the first bottom face 30 and the second bottom face 35 to the first light reception unit 15 is set as A2. A1 is set to be larger than A2. A distance from the boundary line between the first bottom face 30 and the second bottom face 35 to the center of the second light reception unit 16 is set as A3. A3 is set to be equal to a distance ((A1+A2)/2) from a center point of a line segment linking the center of the light source 14 and the center of the first light reception unit 15 to the boundary line between the first bottom face and the second bottom face. In other words, an intermediate position between the second light reception unit 16 and an intermediate position between the light source 14 and the first light reception unit 15 is positioned near the location where the first casing 110 and the second casing 120 are joined by the hinge 130.

A hole portion 111 is provided in the right side face 41 of the first casing 110. A hole portion 112 is provided in the left side face 43 of the first casing 110. A line segment linking the hole portion 111 and the hole portion 112 is parallel to the Y axis. The hole portion 111 and the hole portion 112 are an example of a pair of hole portions. Further, a hole portion 121 is provided in the right side face 44 of the second casing 120. A hole portion 122 is provided in the left side face 46 of the second casing 120. A line segment linking the hole portion 121 and the hole portion 122 is parallel to the Y axis. The hole portion 121 and the hole portion 122 are an example of the pair of hole portions. The hole portion 111, the hole portion 112, the hole portion 121, and the hole portion 122 are holes for inserting pawl portions or the like of a band holder 200, to be described below. As shown in FIGS. 4 and 5, a distance in the X axis direction from the hole portion 111 to the boundary line between the first bottom face 30 and the second bottom face 35 is A3. A distance in the X axis direction from the hole portion 112 to the boundary line between the first bottom face 30 and the second bottom face 35 is A3. A distance in the X axis direction from the hole portion 121 to the boundary line between the first bottom face 30 and the second bottom face 35 is A3. A distance in the X axis direction from the hole portion 122 to the boundary line between the first bottom face 30 and the second bottom face 35 is A3. In other words, an intermediate position between the hole portion 111 and the hole portion 112 is positioned near an intermediate position between the light source 14 and the first light reception unit, and an intermediate position between the hole portion 121 and the hole portion 122 is positioned near the second light reception unit. Further, an intermediate position between the hole portion 111 and the hole portion 121 is positioned near the position of the hinge 130, and an intermediate position between the hole portion 112 and the hole portion 122 is positioned near the position of the hinge 130. The hole portions 111, 112, 121, and 122 are respectively examples of a first hole portion, a second hole portion, a third hole portion, and a fourth hole portion.

As shown in FIG. 6 and so on, in the first casing 110, the distance (the length in the Z axis direction) between the first upper face 20 and the first bottom face 30 gradually decreases in the X axis direction from the lower edge 21 toward the upper edge 23 of the first upper face 20. Likewise in the second casing 120, the distance (the length in the Z axis direction) between the second upper face 25 and the second bottom face 35 gradually decreases in the X axis direction from the upper edge 26 toward the lower edge 28 of the second upper face 25. In other words, the blood flow measurement device 10 gradually becomes thinner from the central part toward the ends in the X axis direction. Thus, the user can fit the blood flow measurement device 10 tightly to the body more easily.

As shown in FIG. 7, the substrate 140, on which components that function as the control unit 11, the wireless communication unit 13, and so on are mounted, and the battery 150, which serves as a power supply source of the blood flow measurement device 10, are disposed in the interior of the blood flow measurement device 10. The substrate 140 is fixed to the first casing 110. The substrate 140 projects from the first casing 110 into the second casing 120 across the hinge 130. The substrate 140 is not fixed to the second casing 120. As shown in FIG. 9, when the first body portion 101 is rotated relative to the second body portion 102, the part of the substrate 140 that projects into the second casing 120 moves within the second casing 120 but does not contact other components or the like due to the space in the interior of the second casing 120. By forming the substrate 140 to project into the second casing 120, a larger substrate can be used without increasing the size of the blood flow measurement device 10. A flexible substrate that deforms in shape as the first body portion 101 rotates may be used as the substrate 140.

(Example of Use)

Figure 10:
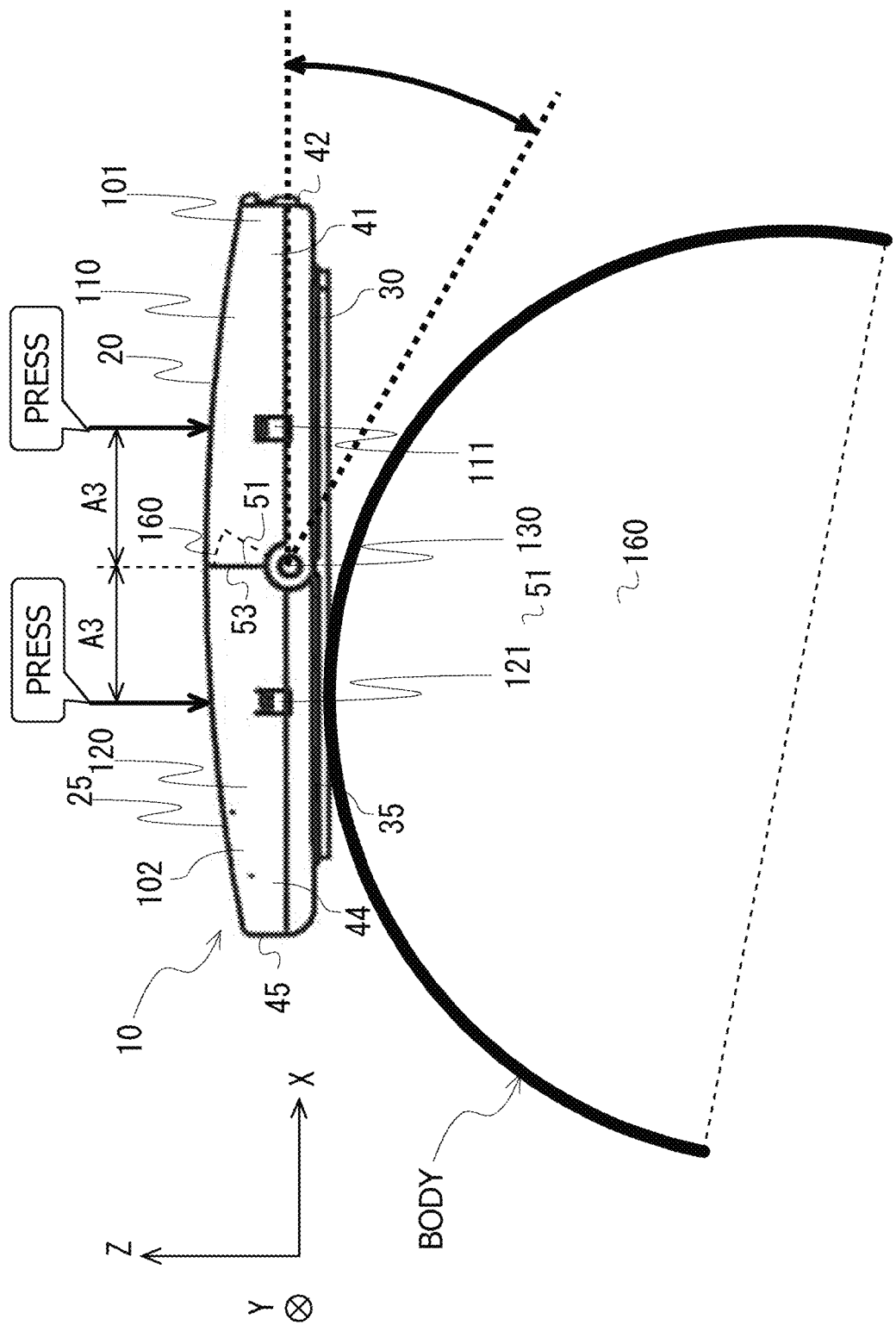
FIG. 10 is a view showing an example of the blood flow measurement device 10 before being tightly fitted to the body.
Figure 11:
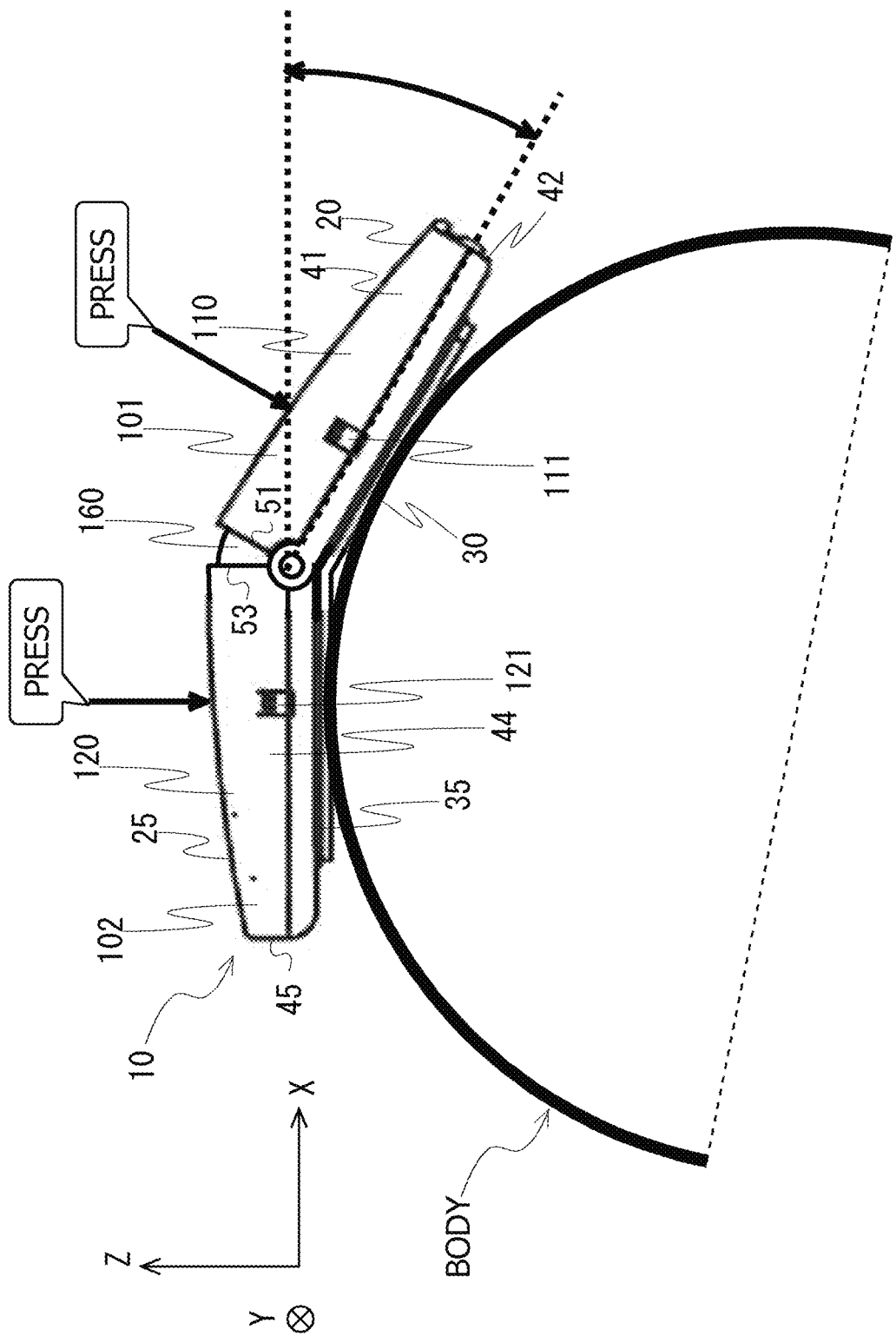
FIG. 11 is a view showing an example of the blood flow measurement device 10 after being tightly fitted to the body.

FIGS. 10 and 11 are views showing an example of use of the blood flow measurement device 10. FIG. 10 is a view showing an example of the blood flow measurement device 10 before being tightly fitted to the body. FIG. 11 is a view showing an example of the blood flow measurement device 10 after being tightly fitted to the body. As shown in FIG. 10, the user fits the first bottom face 30 or the second bottom face 35 of the blood flow measurement device 10 tightly to the measurement subject part (the brain, the arm, the leg, or the like) of the body. Then, using a finger or the like, the user presses the axis linking the hole portion 111 to the hole portion 112 (which is parallel to the Y axis) from the first upper face 20 in the normal direction of the first bottom face 30 and presses the axis linking the hole portion 121 to the hole portion 122 (which is parallel to the Y axis) from the second upper face 25 in the normal direction of the second bottom face 35 toward the body. Thus, as shown in FIG. 11, the first body portion 101 rotates relative to the second body portion 102 such that the bottom face of the blood flow measurement device 10 bends. As a result, the light source 14 and the first light reception unit 15, which exist near the axis linking the hole portion 111 to the hole portion 112, and the second light reception unit 16, which exists near the axis linking the hole portion 121 to the hole portion 122, are tightly fitted to the body. By tightly fitting the light source 14, the first light reception unit 15, and the second light reception unit 16 to the measurement subject part of the body, the blood flow and so on can be measured more accurately. In the blood flow measurement device 10, by setting the distance A3 from the boundary line between the first bottom face 30 and the second bottom face 35 to the center of the second light reception unit 16 to be equal to the distance $((A1+A2)/2)$ from the center point of the line segment linking the center of the light source 14 and the center of the first light reception unit 15 to the boundary line between the first bottom face 30 and the second bottom face 35, the light source 14, the first light reception unit 15, and the second light reception unit 16 can be tightly fitted to the body more easily.

(Band Holder)

In the example described above, the blood flow measurement device 10 is tightly fitted to the body using a finger or the like, but here, an example in which the blood flow measurement device 10 is tightly fitted to the body using a band and a band holder will be described.

Figure 12:
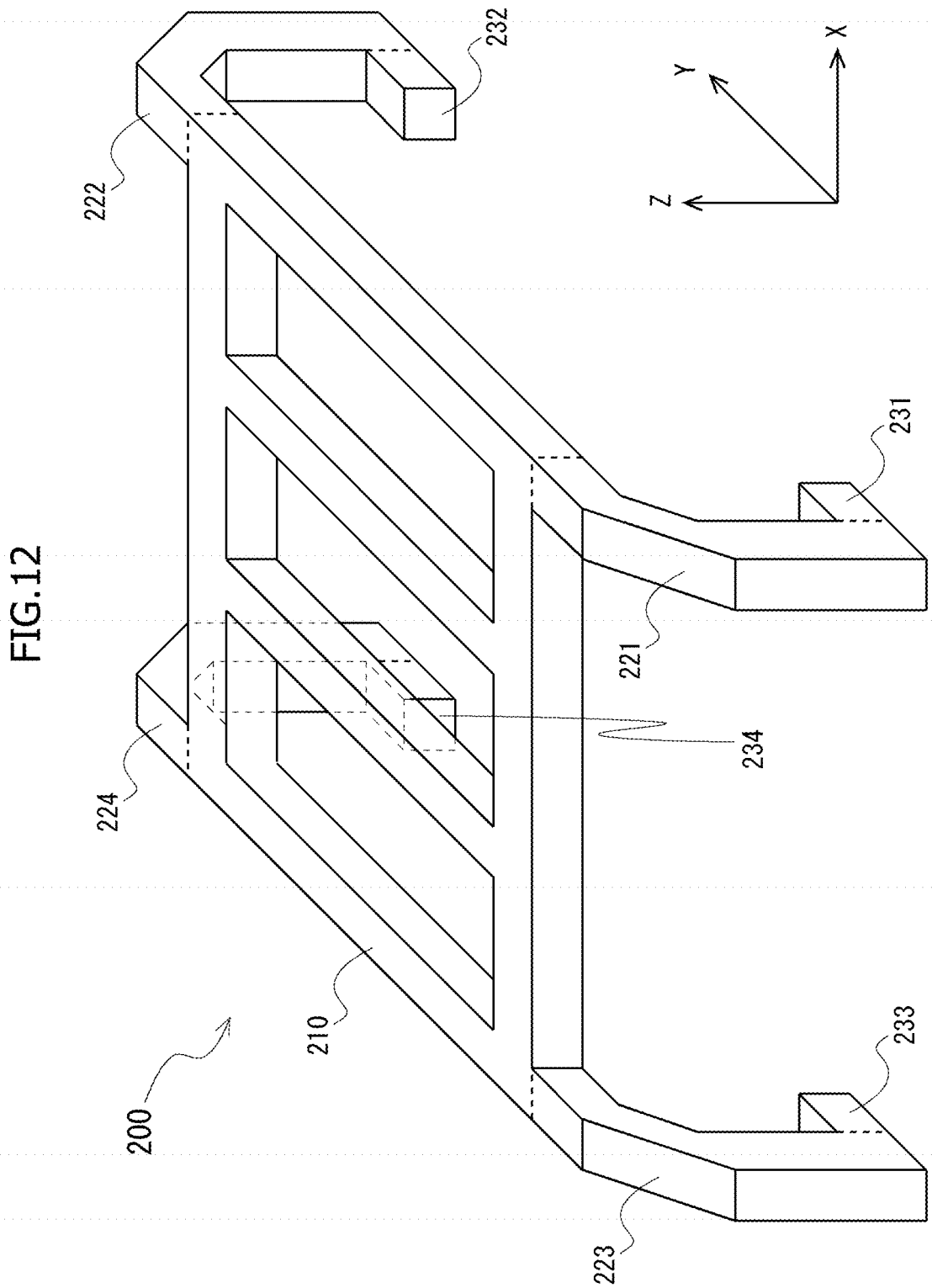
FIG. 12 is a view showing a perspective view of a band holder 200 from above.

FIG. 12 is a view showing a perspective view of the band holder 200 from above. The band holder 200 includes a body portion 210, leg portions 221, 222, 223, 224, and pawl portions 231, 232, 233, 234. The band holder 200 is formed from a resin such as plastic, for example, so as to elastically deform. The body portion 210 has a rectangular planar shape and includes a plurality of opening portions. Each of the leg portions extends toward the outside of the body portion 210 in the Y axis direction from each corner of the body portion 210, is bent in one or more locations, and then extends in the Z axis direction. The band holder 200 is supported by the four leg portions. Further, the pawl portions respectively project inwardly in the Y axis direction from the ends of the leg portions. The positions of the pawl portions correspond respectively to the positions of the hole portions in the blood flow measurement device 10. The pawl portions are fitted respectively into the hole portions in the blood flow measurement device 10.

Figure 13:
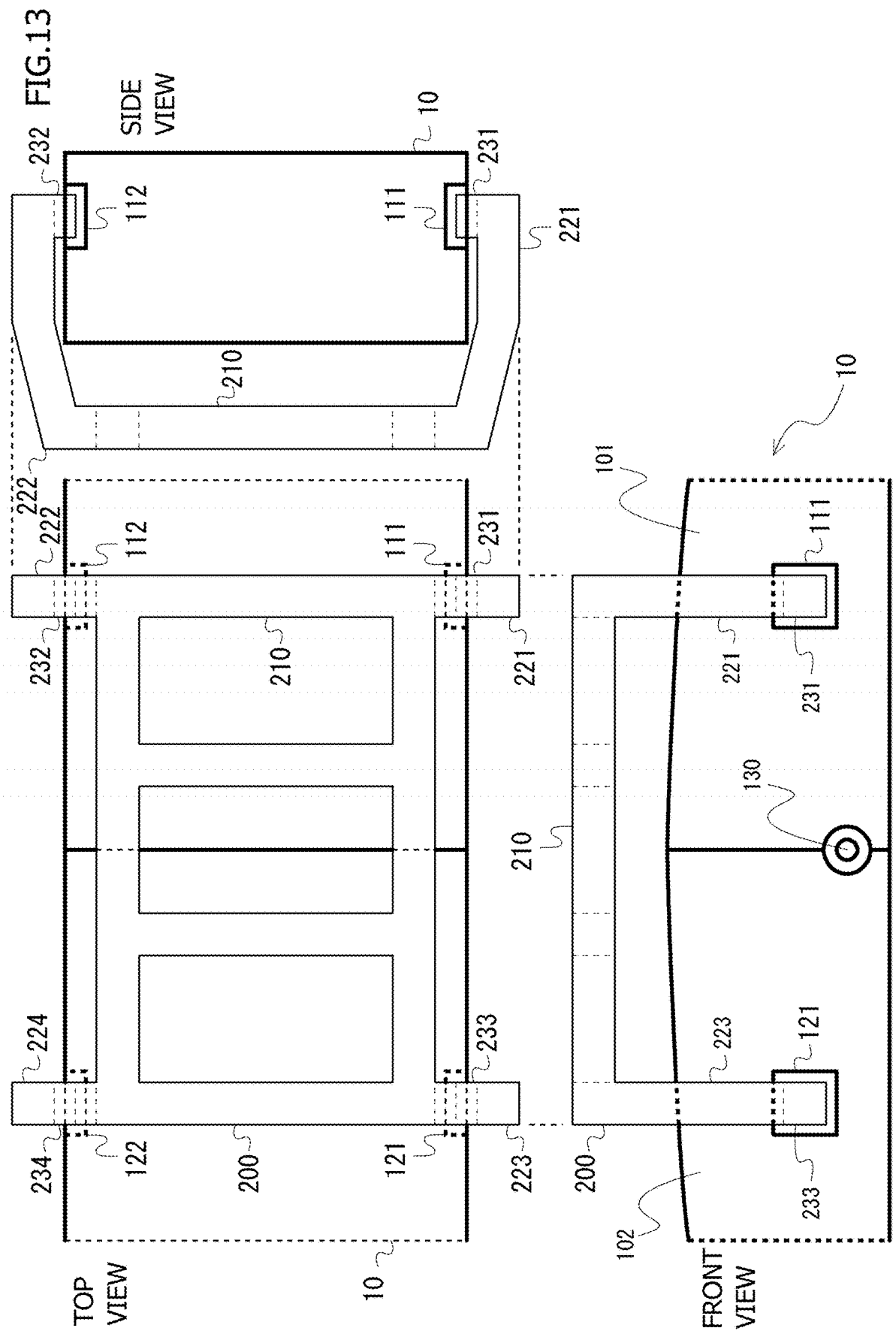
FIG. 13 is a view showing examples of a top view, a front view, and a side view in a case where pawl portions of the band holder 200 are respectively fitted into hole portions in the blood flow measurement device 10.

FIG. 13 is a view showing examples of a top view, a front view, and a side view in a case where the pawl portions of the band holder 200 are fitted respectively into the hole portions in the blood flow measurement device 10. The pawl portion 231 is fitted into the hole portion 111, the pawl portion 232 is fitted into the hole portion 112, the pawl portion 233 is fitted into the hole portion 121, and the pawl portion 234 is fitted into the hole portion 122. Even when the first body portion 101 of the blood flow measurement device 10 is rotated relative to the second body portion 102, due to the elastic deformation of the band holder 200, the pawl portions fitted respectively into the hole portions do not become detached from the hole portions.

Figure 14:
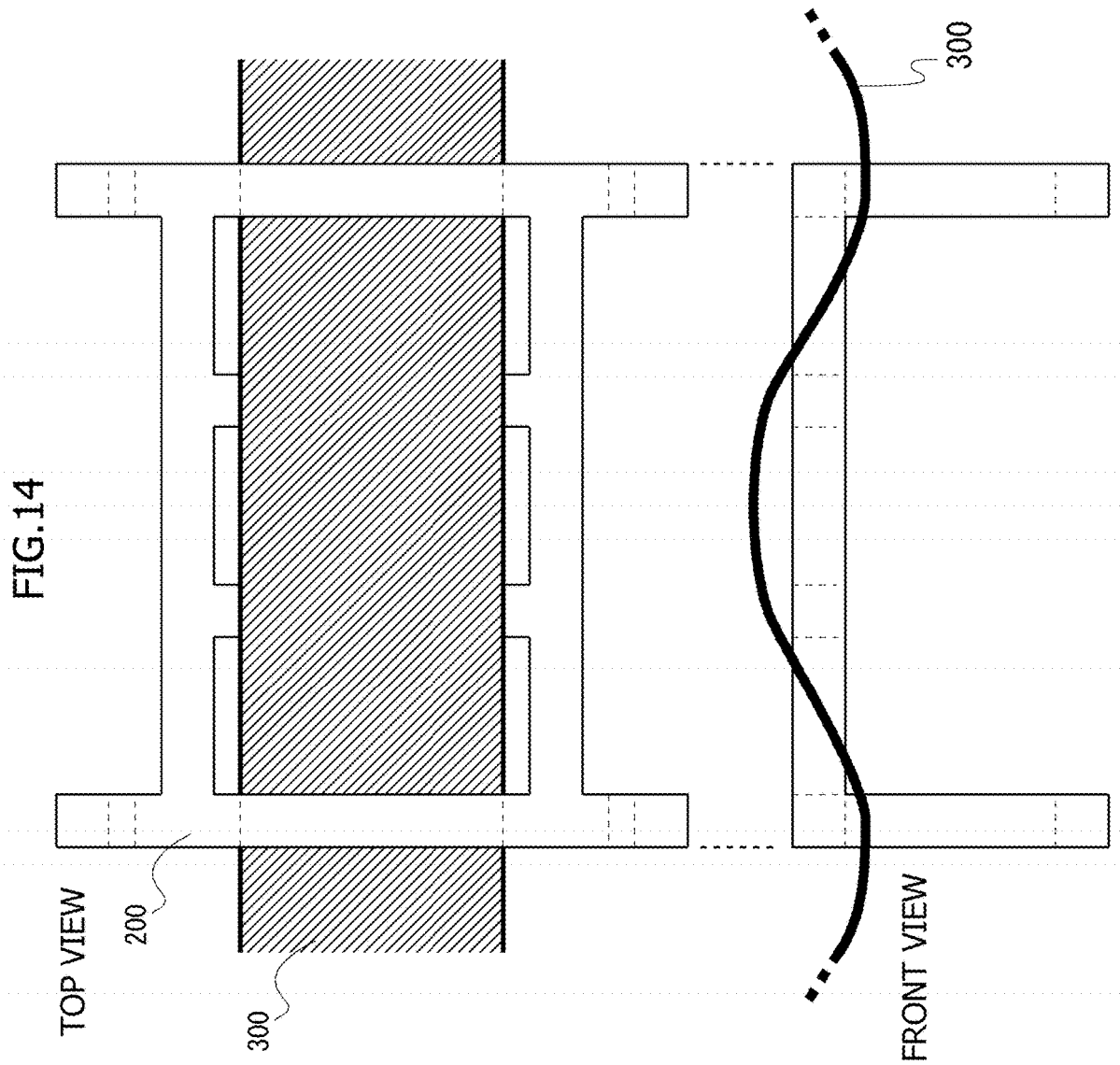
FIG. 14 is a view showing examples of a top view and a front view in a case where a band 300 is attached to the band holder 200.

FIG. 14 is a view showing examples of a top view and a front view in a case where a band 300 is attached to the band holder 200. The band 300 is a member that is wound around and thereby fixed to the body of the user. The band 300 is made of fabric, rubber, or the like, for example. The blood flow measurement device 10 is fixed to the body of the user by the band 300 and the band holder 200. The band 300 is passed through the opening portions in the body portion 210 of the band holder 200 so as to be sewn into the body portion 210. The band 300 is thus attached to the band holder 200. After attaching the band 300 to the band holder 200, the blood flow measurement device 10 is attached to the band holder 200, as shown in FIG. 11. Further, by winding the band 300, to which the band holder 200 and the blood flow measurement device 10 are attached, fixedly around the body of the user, the blood flow measurement device 10 is attached to the body of the user. By fixing the band 300 to the body of the user, the band holder 200 and the blood flow measurement device 10 are pressed against the body of the user. The pawl portions of the band holder 200 are respectively fitted into the hole portions of the blood flow measurement device 10. Thus, similarly to the examples shown in FIGS. 10 and 11, when the band holder 200 is pressed against the body by the band 300, the axis linking the hole portion 111 to the hole portion 112 is pressed in the normal direction of the first bottom face from the first upper face, and the axis linking the hole portion 121 to the hole portion 122 is pressed against the body in the normal direction of the second bottom face from the second upper face. As a result, the light source 14 and the first light reception unit 15, which exist near the axis linking the hole portion 111 to the hole portion 112, and the second light reception unit 16, which exists near the axis linking the hole portion 121 to the hole portion 122, are tightly fitted to the body.

By using the band holder 200 and the band 300 with the blood flow measurement device 10 attached thereto, the user can attach the blood flow measurement device 10 to the body without pressing the blood flow measurement device 10 with a finger or the like.

Instead of using the band holder 200 and the band 300, the blood flow measurement device 10 may be attached to the body by attaching the pawl portions that are respectively fitted into the hole portions of the blood flow measurement device 10 directly to the band 300, fitting the pawl portions into the hole portions, and then winding the band 300 around the body of the user fixedly.

Note that in order to attach the band 300 or the band holder 200 to the blood flow measurement device 10, a structure other than the hole portions 111, 112, 121, 122 may be used. For example, recessed portions or steps with which latch portions provided on the band holder 200, the band 300, or the like are engaged may be provided on the blood flow measurement device 10 on the right side face 41 and the left side face 43 between the first bottom face 30 and the first upper face 20 and on the right side face 44 and the left side face 46 between the second bottom face 35 and the second upper face 25. The latch portions provided on the band holder 200, the band 300, or the like may be structures such as the pawl portions described in the above embodiment or any other structure that can be engaged with or fitted to a hole portion, a recessed portion, a step, or the like. For example, hole portions, recessed portions, steps, or the like may be provided in the band holder 200, pawl portions, projecting portions, or the like may be provided on the aforementioned side faces of the blood flow measurement device 10, and the band holder 200 may be latched, engaged, or fitted to the pawl portions, projecting portions, or the like on the aforementioned side faces of the blood flow measurement device 10.

(Handy Holder)

Here, an example in which the blood flow measurement device 10 is tightly fitted to the body by a handy holder for fixing the fingers of the user will be described.

Figure 15:
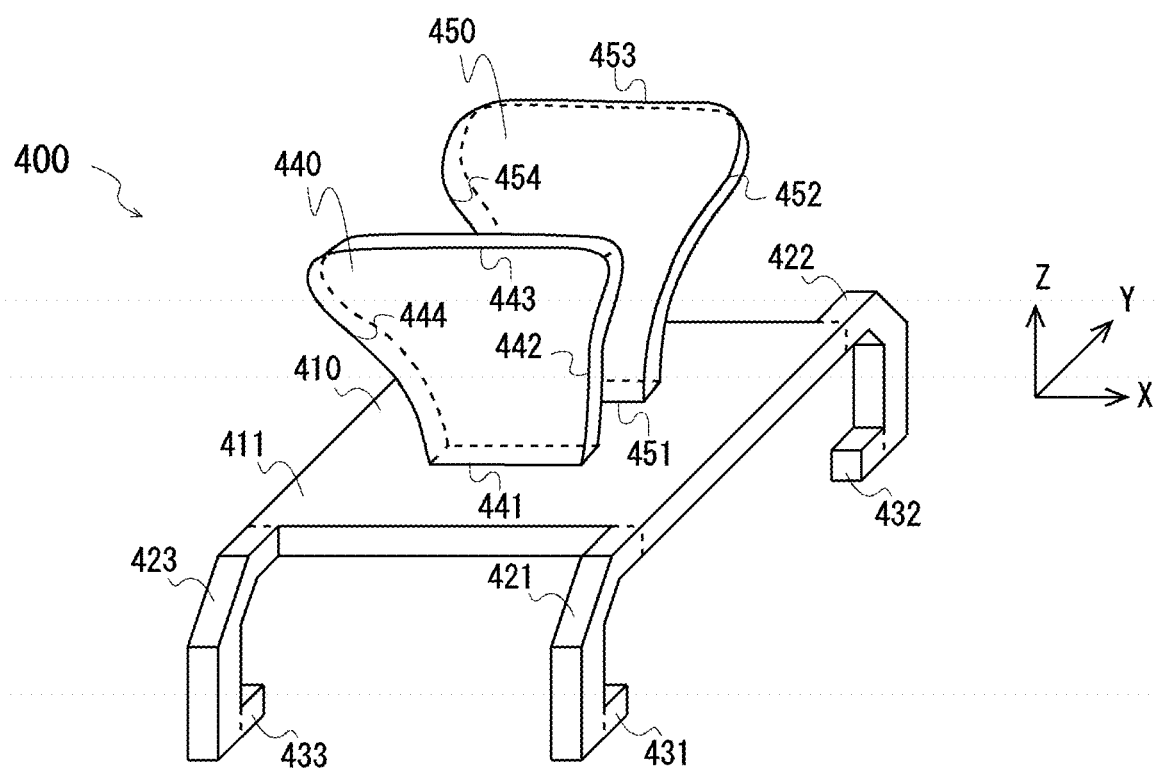
FIG. 15 is a view showing a perspective view of a handy holder 400 from above.

FIG. 15 is a view showing a perspective view of the handy holder 400 from above. The handy holder 400 includes a body portion 410, leg portions 421, 422, 423, 424, pawl portions 431, 432, 433, 434, and wing portions 440, 450. The handy holder 400 is formed from a resin such as plastic, for example, so as to elastically deform. The body portion 410 has a rectangular planar shape. In FIG. 15, a surface on which the body portion 410 is visible is set as an upper face 411 of the body portion 410. Each of the leg portions extends toward the outside of the body portion 410 in the Y axis direction from each corner of the body portion 410, is bent in one or more locations, and then extends in the Z axis direction. The handy holder 400 is supported by the four leg portions. Further, the pawl portions respectively project inwardly in the Y axis direction from the ends of the leg portions. The positions of the pawl portions correspond respectively to the positions of the hole portions in the blood flow measurement device 10. Similarly to the band holder 200 described above, the pawl portions of the handy holder 400 are fitted respectively into the hole portions in the blood flow measurement device 10. The leg portions 421, 422, 423, 424 and the pawl portions 431, 432, 433, 434 of the handy holder 400 are similar to the leg portions 221, 222, 223, 224 and the pawl portions 231, 232, 233, 234 of the band holder 200.

The wing portion 440 and the wing portion 450 are disposed on the upper face 411 of the body portion 410. The wing portions 440, 450 are both planar. The wing portion 440 and the wing portion 450 have similar shapes. The wing portion 440 has a bottom edge 441, a right side edge 442, an upper edge 443, and a left side edge 444. The bottom edge 441 is an edge disposed substantially parallel to the X axis near the center of the upper face 411 of the body portion 410. The right side edge 442 is an edge that forms the right side of the wing portion 440 when looking in the direction of the leg portions 222, 224 from the leg portions 221, 223. Further, the left side edge 444 is an edge that forms the left side of the wing portion 440 when looking in the direction of the leg portions 222, 224 from the leg portions 221, 223. The upper edge 443 is the edge of the wing portion 440 that opposes the bottom edge 441. The wing portion 440 stands upright at a right angle to the upper face 411 of the body portion 410 and curves outwardly (frontward in FIG. 15) relative to the body portion 410 from the bottom edge 441 toward the upper edge 443. Further, the width of the wing portion 440 increases from the bottom edge 441 toward the upper edge 443. The wing portion 450 has a bottom edge 451, a right side edge 452, an upper edge 453, and a left side edge 454. The bottom edge 451 is tan edge disposed substantially parallel to the X axis near the center of the upper face 411 of the body portion 410. The right side edge 452 is an edge that forms the right side of the wing portion 450 when looking in the direction of the leg portions 222, 224 from the leg portions 221, 223. Further, the left side edge 454 is an edge that forms the left side of the wing portion 450 when looking in the direction of the leg portions 222, 224 from the leg portions 221, 223. The upper edge 453 is the edge of the wing portion 450 that opposes the bottom edge 451. The wing portion 450 stands upright at a right angle to the upper face 411 of the body portion 410 and curves outwardly (rearward in FIG. 15) relative to the body portion 410 from the bottom edge 451 toward the upper edge 453. Further, the width of the wing portion 450 increases from the bottom edge 451 toward the upper edge 453.

When using the handy holder 400, the user places two adjacent fingers (the index finger and the middle finger, for example) on the upper face 411 of the body portion 410 so that the two fingers are respectively substantially parallel to the outside of the bottom edge 441 of the wing portion 440 and the outside of the bottom edge 451 of the wing portion 450. At this time, the two adjacent fingers are substantially parallel to the X axis. By inserting one of the two adjacent fingers between the vicinity of the upper edge 443 of the wing portion 440 and the body portion 410 and inserting the other finger between the vicinity of the upper edge 453 of the wing portion 450 and the body portion 410, the user can hold the handy holder 400 with stability.

Further, when using the handy holder 400, the user may place two adjacent fingers on the upper face 411 of the body portion 410 so that one of the adjacent fingers is beside the right side edge 442 of the wing portion 440 and the right side edge 452 of the wing portion 450 and the other is beside the left side edge 444 of the wing portion 440 and the left side edge 454 of the wing portion 450. At this time, the two adjacent fingers are substantially parallel to the Y axis. At this time, the user can hold the handy holder 400 with stability by gripping the wing portions 440, 450 between two adjacent fingers. Using the wing portions 440, 450, the positions of the fingers holding the handy holder 400 can be changed to positions in which the handy holder 400 is easier to hold in accordance with the position in which the blood flow measurement device 10 is to be fixed to the body.

(Actions and Effects of Embodiment)

The blood flow measurement device 10 includes the first body portion 101, the second body portion 102, and the hinge 130 for connecting the first body portion 101 to the second body portion 102. The first body portion 101 is rotated relative to the second body portion 102 by the hinge 130. In the blood flow measurement device 10, the distance A3 from the boundary line between the first bottom face 30 and the second bottom face 35 to the center of the second light reception unit 16 is set to be equal to the distance ((A1+A2)/2) from the center point of the line segment linking the center of the light source 14 and the center of the first light reception unit 15 to the boundary line between the first bottom face 30 and the second bottom face 35. As a result, when the user or the like presses the blood flow measurement device 10 in the normal direction of the respective bottom faces from the first upper face 20 and the second upper face 25, the light source 14, the first light reception unit 15, and the second light reception unit 16 can be tightly fitted to the body easily.

By winding the band holder 200 and the band 300, to which the blood flow measurement device 10 is attached, around the body, the blood flow measurement device 10 can be attached to the body without the need for the user to press the blood flow measurement device 10 with a finger or the like.

By employing the handy holder 400 to which the blood flow measurement device 10 is attached, the blood flow measurement device 10 can be fixed to the body with greater stability.

The configurations described above may be implemented in any possible combinations.

<Computer-Readable Recording Medium>

A program for realizing any of the functions described above on a computer or another machine or device (hereafter, a computer or the like) can be recorded on a recording medium that can be read by a computer or the like. By causing the computer or the like to read and execute the program recorded on the recording medium, the function can be provided.

Here, a recording medium that can be read by a computer or the like is a recording medium that can store information such as data or a program by means of an electrical, magnetic, optical, mechanical, or chemical action, and can be read from a computer or the like. Constituent elements of a computer, such as a CPU and a memory, may be provided in the recording medium, and the CPU may be caused to execute the program.

Further, examples of recording media that can be detached from the computer or the like include a flexible disk, a magneto-optical disk, a CD-ROM, a CD-R/W, a DVD, a DAT, 8 mm tape, a memory card, and so on.

Furthermore, a hard disk, a ROM, or the like are available as recording media that are fixed to the computer or the like.

REFERENCE SIGNS LIST

10 Blood flow measurement device
11 Control unit
13 Wireless communication unit
14 Light source
15 First light reception unit
16 Second light reception unit
20 First upper face
25 Second upper face
30 First bottom face
35 Second bottom face
41 Right side face of first casing
42 Upper side face of first casing
43 Left side face of first casing
44 Right side face of second casing
45 Lower side face of second casing
46 Left side face of second casing
101 First body portion
102 Second body portion
110 First casing
111 Hole portion
112 Hole portion
120 Second casing
121 Hole portion
122 Hole portion
130 Hinge
140 Substrate
150 Battery
160 Cover portion
200 Band holder
210 Body portion
221 Leg portion
222 Leg portion
223 Leg portion
224 Leg portion
231 Pawl portion
232 Pawl portion
233 Pawl portion
234 Pawl portion
300 Band
400 Handy holder
410 Body portion
411 Upper face
421 Leg portion
422 Leg portion
423 Leg portion
424 Leg portion
431 Pawl portion
432 Pawl portion
433 Pawl portion
434 Pawl portion

What is claimed is:

1. A blood flow measurement device comprising a first body portion, a second body portion, and a hinge, wherein
the first body portion includes a first casing having a first bottom face, a light source that emits near-infrared radiation from the first bottom face to the outside of the first casing, and a first photoelectric element that receives the near-infrared radiation from the first bottom face side on the outside of the first casing,
the second body portion includes a second casing having a second bottom face, and a second photoelectric element that receives the near-infrared radiation that is emitted by the light source of the first body portion from the second bottom face side on the outside of the second casing, and
the hinge joins the first body portion to the second body portion so as to make an angle formed by the first bottom face and the second bottom face variable,
wherein when a distance from a boundary line between the first bottom face and the second bottom face to the light source is A1, a distance from the boundary line to the first photoelectric element is A2, and a distance from the boundary line to the second photoelectric element is A3,
the light source and the first photoelectric element are arranged in the first body portion, and the second photoelectric element is arranged in the second body portion so that a relationship of a formula "(A1+A2)/2=A3" is satisfied,
wherein a distance from a first upper face to the first bottom face of the first body portion near the hinge is longer than a distance from the first upper face to the first bottom face of an edge of the first body portion and a distance from the second upper face to the second bottom face of the second body portion near the hinge is longer than a distance from the second upper face to the second bottom face of an edge of the second body portion.

2. The blood flow measurement device according to claim 1, wherein the hinge is arranged at or near the boundary line.

3. The blood flow measurement device according to claim 2, wherein
the first casing includes a first right side face and a first left side face, which are connected to the first bottom face and oppose each other,
the second casing includes a second right side face and a second left side face, which are connected to the second bottom face and oppose each other,
the first right side face and the first left side face respectively include a first hole portion and a second hole portion,
the second right side face and the second left side face respectively include a third hole portion and a fourth hole portion,
an intermediate position between the first hole portion and the second hole portion is positioned near the intermediate position between the light source and the first photoelectric element,
an intermediate position between the third hole portion and the fourth hole portion is positioned near the position of the second photoelectric element,
an intermediate position between the first hole portion and the third hole portion is positioned near the position of the hinge, and
an intermediate position between the second hole portion and the fourth hole portion is positioned near the position of the hinge,
wherein a distance from the hinge to an intermediate position between the first hole portion and the second hole portion is A3 and a distance from the hinge to an intermediate position between the third hole portion and the fourth hole portion is A3.

4. The blood flow measurement device according to claim 1, comprising a substrate that is fixed to the first bottom face inside the first casing, wherein
the substrate projects from the first body portion into the second body portion.

* * * * *